United States Patent [19]

Fenstermaker et al.

[11] 4,197,271
[45] Apr. 8, 1980

[54] AIR FRESHENER

[75] Inventors: Michael Fenstermaker, Lynwood; James Tucker, Manhattan Beach, both of Calif.

[73] Assignee: Orion Industries, Inc., Compton, Calif.

[21] Appl. No.: 962,390

[22] Filed: Nov. 20, 1978

[51] Int. Cl.² ............................ A61L 9/01; A61L 9/04
[52] U.S. Cl. .................................... 422/123; 239/56; 422/4; 422/306
[58] Field of Search ................. 422/4, 123, 306; 239/57, 58, 59, 60, 56

[56] References Cited

U.S. PATENT DOCUMENTS

| | | | |
|---|---|---|---|
| 2,765,194 | 10/1956 | Will | 239/60 X |
| 2,797,844 | 7/1957 | Meek | 239/60 X |
| 3,595,607 | 7/1971 | Gores | 422/123 |
| 3,754,707 | 8/1973 | Morane | 239/59 |
| 3,784,102 | 1/1974 | Stults | 239/57 X |
| 3,804,330 | 4/1974 | Miller et al. | 239/60 X |
| 3,836,077 | 9/1974 | Skildum | 239/60 |
| 3,844,478 | 10/1974 | Davis | 239/60 X |
| 3,902,877 | 9/1975 | Swaim | 422/123 X |
| 3,976,246 | 8/1976 | Hauri et al. | 239/60 X |
| 4,014,501 | 3/1977 | Buckenmayer | 239/58 |

FOREIGN PATENT DOCUMENTS

| | | | |
|---|---|---|---|
| 524042 | 7/1940 | United Kingdom | 239/57 |
| 1497580 | 1/1978 | United Kingdom | 239/58 |
| 1514712 | 6/1978 | United Kingdom | 422/123 |

*Primary Examiner*—Barry S. Richman
*Attorney, Agent, or Firm*—Fulwider, Patton, Rieber, Lee & Utecht

[57] ABSTRACT

An air freshener for use, for example, in an automotive vehicle in which an annular scented pad is disposed within a hollow housing formed of mating, shallow, pan-shaped tray sections. One of the tray sections includes an annular axial hub. The other tray section has a guide extending outward therefrom and engageable with the hub to releasably secure the tray sections together with the scented pad entrapped therein. A restraining ridge about the hub holds the pad in position. A double sided pressure sensitive adhesive is fastened to one of the tray sections and is used to secure the housing to a surface within the atomotive vehicle in immobile fashion.

3 Claims, 3 Drawing Figures

AIR FRESHENER

BACKGROUND OF THE INVENTION

1. Field of the Invention

A present invention relates to air freshening devices useful for overcoming objectionable odors in confined locations, especially the passenger occupancy areas of automotive vehicles.

2. Description of the Prior Art

In the past, air freshening devices have been used extensively to suppress objectionable odors present in automotive vehicles as well as other confined areas. Porous articles impregnated with scented chemicals are typically located in the passenger occupancy areas of automotive vehicles, and effectively overcome unpleasant odors produced by smoking materials, mildew, dampness, and exhaust and hydrocarbon fumes. Typical scented deodorizers are packaged within a cloth or paper wrapping and are suspended within the vehicle, frequently from the stem of the rear view mirror. However, when a deodorizer pad dangles in this fashion, it often presents a distraction to the vehicle operator. The sporadic movement of an article hanging from the rearview mirror draws the attention of the operator from the road and other traffic conditions and toward the movement of the deodorizer. Furthermore, because a deodorizer located in this fashion is suspended in front of the windshield, it acts as a visual obstruction to the vehicle operator. As a result, conventional automotive vehicle cab deodorizers subject the vehicle operator and other passengers to unnecessary visual fatigue, and are indeed a traffic hazard.

SUMMARY OF THE INVENTION

The present invention is directed to a deodorizer apparatus which can be placed in an automotive vehicle or in some other confined location, such as a bathroom or a closet. The deodorizer apparatus can be placed in an unobtrusive location, but in a manner in which it can still be effective. The scented element of the deodorizer of the invention is located in a disk-shaped housing having opposing shallow concave sections which meet in face to face fashion to define a cavity therebetween and which can be quickly locked and unlocked by rotation and counter-rotation relative to each other. One of the concave trays is equipped with a central axial annular hub about which a flat annular deodorizer impregnated pad is positioned. A guide extends from the other tray near its center and passes through the hub and seats in a latching arrangement relative thereto. The tray sections are twisted together to bring a catch on the guide into engagement with an overhanging shoulder at the interior of the hub so that the tray sections are thereby drawn together to define a hollow enclosure for the scented annular pad.

Preferably, the outer rims of the tray sections are shaped in a mating saw-tooth configuration with corresponding abutments that meet when the trays are rotated together and when the catch of the guide of one tray rides to the deepest point of engagement with the internal shoulder of the hub of the other tray. Preferably also, at least one of the trays is equipped with a double faced pad of pressure senstive adhesive. This allows the housing to be mounted decoratively and immovably on either a horizontal or vertical surface, facing either up, down or sideways. Air can thereby circulate freely through the air freshener housing, but the housing itself does not present a visual obstruction or exhibit distracting movement.

The invention can be described with greater clarity and particularity by reference to the accompanying drawings.

DESCRIPTION OF THE EMBODIMENT

Figure 1:
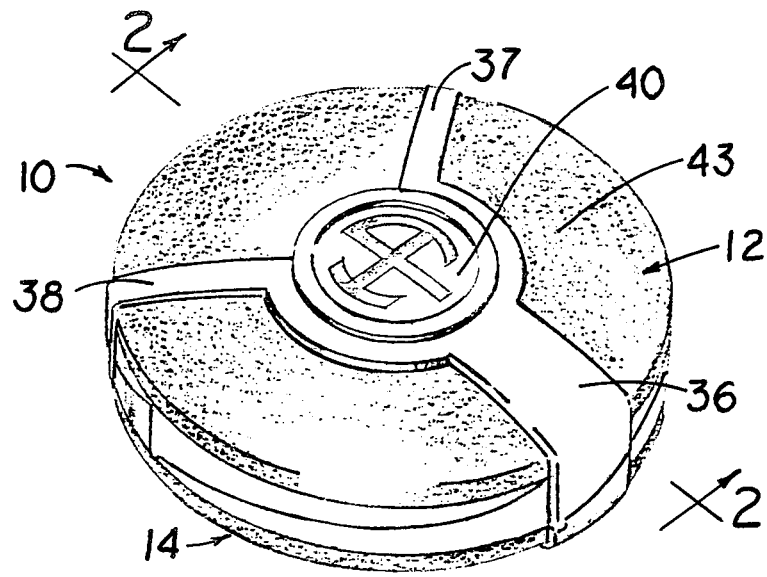
FIG. 1 is a perspective view of an embodiment of the air freshener housing of the invention.

FIG. 1 illustrates a portable air freshener 10 which has a generally disk-shaped housing formed by a pair of opposing circular, shallow, concave pan-shaped trays 12 and 14. As noted in FIG. 2, the trays 12 and 14 cooperate to define a generally disk-shaped cavity therebetween and both have mating circular annular rims 16 and 18 respectively which are serrated in a sawtooth configuration. The curved rim 16 of the tray 12 has four spiral inclines 20, each of which culminates in a downwardly depending sawtooth 22 having a vertical abutment facing in one direction. The rim 18 of the other tray 14 likewise is formed in a sawtooth configuration in which four spiral inclines 24 extend between vertical abutments facing in the opposite direction to define upwardly directed sawteeth 26. At the center of the tray 12, visible in FIGS. 2 and 3, and annular hub 28, having an outer surface shaped generally as a fustrum of a cone, depends downwardly toward the opposing tray 14. A flat, annular scented pad 32 is disposed about the outer circumference of the hub 28 and is held in position on the hub 28 by a radially outwardly directed circumferential retaining ridge 34, visible in FIGS. 2 and 3. Upright guide posts 30 with outwardly directed catches 48 extend through the interior of the hub 28 to maintain the trays 12 and 14 in coaxial alignment.

The tray 12 has an exterior matte finish and includes embossed radial spoke-like projections 36, 37 and 38 formed across its top surface in relief above the matte background and down the sides of the rim 16. An emblem 40 is defined in relief at the intersection of the radial spokes 36,37 and 38.

Figure 2:
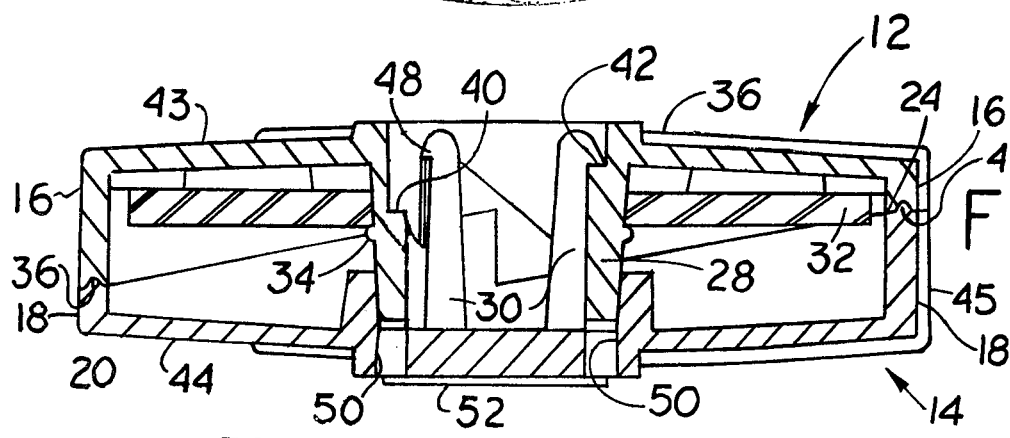
FIG. 2 is a sectional view taken along the lines 2—2 of FIG. 1.

The slightly domed expansive, disk-shaped upper surface 43 of the tray 12 curves at its perimeter to define the annular outer rims 16, as depicted in FIG. 2. The rim 16 encircles the central hub 28 in a vertical zig-zag pattern visible in FIGS. 1 and 3. The downwardly extending edge 20 of the rim 16 is grooved with a channel, as indicated at 36 in FIG. 2, to facilitate positioning of the opposing rim 18 of the tray 14.

The downwardly depending annular hub 28 at the center of the tray 14 narrows slightly in the direction away from the surface 43 of the tray 12 and is formed generally in the shape of a truncated cone. The circumferential ridge 34 encircling the hub 28 at about its vertical midsection is utilized to capture and hold the scented annular pad 32 in position about the hub 28. A spirally inclined shoulder is defined into the otherwise smooth cylindrical surface of the inner wall at the interior of the hub 28. The shoulder extends through an arc of about 110 degrees from a lowermost horizontal ledge 40 in FIG. 2 to an uppermost raised landing 42. The angular rotation between trays 12 and 14 corresponds to the angular distance between adjacent sawteeth, being less than the 110° due to the thickness of guide ports 30 which abut vertical faces in hub 28.

The opposing tray 14 is equipped likewise with a slightly domed expansive disk shaped surface 44 at the periphery of which the upturned circular rim 18 is defined. Corresponding embossed radial spokes 45 turn upwardly on the rim 18 to meet the downwardly directed extremities of the spokes 36, 37 and 38. The edge 24 of the rim 18 directed toward the tray 12 is equipped with a centrally located upwardly directed ridge 46 which resides within the channel 36 of the rim 16 of the tray 12. The rims 16 and 18 are thereby maintained in coaxial alignment by the interaction of the ridge 46 with the channel 36.

At the center of the tray 14, there are three upstanding elongated guide legs 30, each equipped with an outwardly directed overhanging catch 48. The guide legs 30 rise from the floor of the tray 14, but utilize the outwardly directed catches 48 to interlock with the spirally inclined shoulder in the interior wall of the hub 28 to maintain the trays 12 and 14 in fixed disposition relative to each other.

Figure 3:
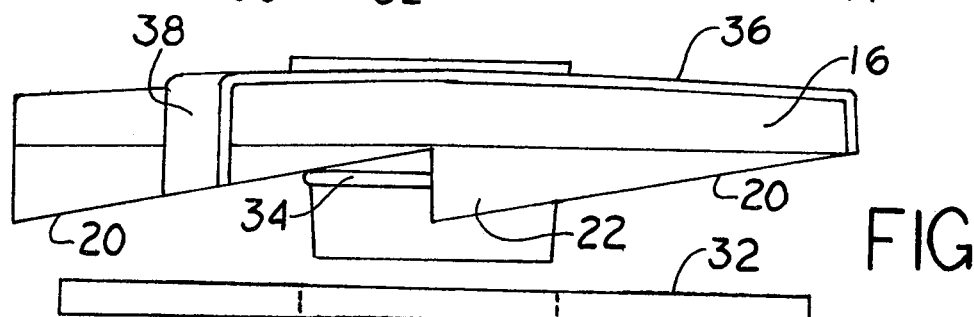
FIG. 3 is an exploded elevational view of the air freshener components.
Figure 3:
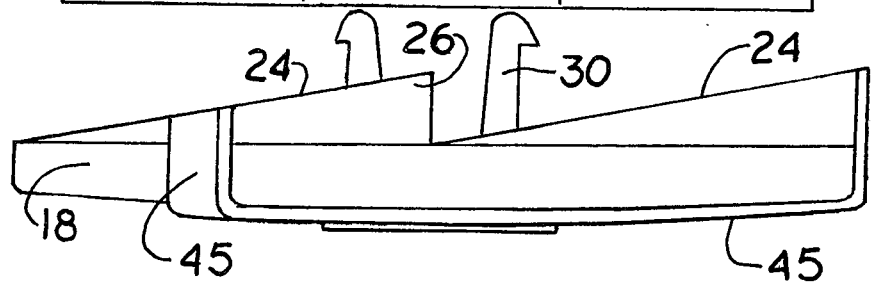

The annular scented pad 32 which fits about the hub 28 and is captured by the annular ridge 34 is visible in FIG. 3. This pad is impregnated with some conventional odor absorbant or perfume to alleviate the undesirable smell of unwanted odors carried in ambient air. These odors are most objectionable in confined places and are particularly prevalent in the passenger enclosures of automotive vehicles. Air is allowed to circulate through the air holes 50 located in the lower surface 44 of the tray 14 radially outwardly and exteriorally from the guides 30, and also through the interstices between the mating edges of the rims 16 and 18 when trays 12 and 14 are rotated to their open position. A pressure sensitive adhesive pad 52, having adhesive on both sides, is formed in the shape of a flat disk, and is pressed against the underside of the tray 14 in axial alignment with the center of the housing of the air freshener 10. The exposed surface of the adhesive pad 52 can then be pressed against a vehicle dashboard, door panel, or other location within the passenger compartment of a vehicle. The air freshener 10 may thereby be positioned in virtually any location so as to be unobstrusive to the vehicle occupants. Nevertheless, because of its rigid construction and compact design, the air freshener 10 will not be accidentally torn or mutilated. Moreover, since the air freshener 10 can be positioned away from the windshield area, it presents no safety hazard to the vehicle operator.

To assemble the air freshener 10, an annular scented pad 32 is pressed inwardly on the hub 28. The pad 32 is resilient enough so that it can be forced past the circumferential ridge 34 which extends about the outer periphery of the hub 28. Once the scented pad 32 is in position, the ridge 34 holds it immobile.

The trays 12 and 14 are then oriented in axially alignment in longitudinal displacement and off-set 90 degrees from the positions depicted in FIGS. 1 and 3. The trays 12 and 14 are then pressed toward each other and rotated toward engagement with the spirally inclined edges 20 and 24 residing in contact with each other. The circumferential ridges 46 travel within the channels 36 until the sawteeth 22 and 26 of the trays 12 and 14 respectively meet in abutting relationship. At the same time, the guide posts 30 travel in rotation relative to the hub 28 from an initial position with the catch 48 in longitudinal displacement from the ledge 40 to a position in which the catch 48 bears against the landing 42 at the opposite end of the spirally inclined shoulder. In this position, the trays 12 and 14 are releasably locked together, and will remain together to define a hollow housing for the scented pad 32 until such time as they are intentionally counter-rotated and separated from each other. When the housing formed by the trays 12 and 14 has been closed, the exposed surface of the adhesive pad 52 can be pressed to any article upon which it is desired to mount the air freshener 10.

It is apparent that numerous variations and modifications of the invention will become apparent to those familiar with air fresheners. Consequently, the scope of the invention should not be construed as limited to the specific embodiment disclosed, but rather is defined in the claims appended hereto.

We claim:

1. A portable air freshener comprising a housing with a cavity formed between a pair of opposing concave trays both having mating circular annular rims, a first of said trays having an axial hub projecting into the concavity of a second of said trays, said hub having outer restraining means and an interior shoulder within said hub which is spirally inclined, an annular removable scented pad disposed concentrically about said hub in said cavity and maintained thereon by said restraining means, and said second of said trays having guide means interiorally disposed relative to said hub for centering said second tray relative to said first tray, said guide means having a resilient outwardly biased catch engaging said shoulder of said hub, whereby relative twisting of said first and second trays together carries said catch up said inclined shoulder, thereby drawing said trays together.

2. An air freshener according to claim 1 further characterized in that said annular rims are shaped in mating sawtooth configurations with a plurality of spiral inclines each formed to cover an arc.

3. An air freshener according to claim 2 further characterized in that the edges of one of said mating rims has a channel formed therein and the other of said edges has a ridge defined therein which resides within said channel to hold said edges transversely immobile.

* * * * *

Disclaimer

4,197,271.—*Michael Fenstermaker*, Lynwood; and *James Tucker*, Manhattan Beach, both of Calif. AIR FRESHENER.Patent dated Apr. 8, 1980. Disclaimer filed Mar. 29, 1989, by the assignee, Mr. Gasket Co.

Hereby enters this disclaimer to the entire term of said patent.
[*Official Gazette May 23, 1989*]